United States Patent
Laldas et al.

(10) Patent No.: US 11,191,791 B2
(45) Date of Patent: Dec. 7, 2021

(54) PREPARATION OF DRY FORMULATIONS OF DAIRY PROBIOTICS

(71) Applicant: PRAJ INDUSTRIES LIMITED, Pune (IN)

(72) Inventors: Sharad Krishnachandra Laldas, Hinjewadi (IN); Aamod Anil Natu, Hinjewadi (IN); Aarohi Atul Kulkarni, Hinjewadi (IN)

(73) Assignee: PRAJ INDUSTRIES LIMITED, Pune (IN)

( * ) Notice: Subject to any disclaimer, the term of this patent is extended or adjusted under 35 U.S.C. 154(b) by 74 days.

(21) Appl. No.: 16/484,952

(22) PCT Filed: Feb. 7, 2018

(86) PCT No.: PCT/IN2018/050062
§ 371 (c)(1),
(2) Date: Aug. 9, 2019

(87) PCT Pub. No.: WO2018/154593
PCT Pub. Date: Aug. 30, 2018

(65) Prior Publication Data
US 2019/0358272 A1    Nov. 28, 2019

(30) Foreign Application Priority Data

Feb. 22, 2017  (IN) ............... 201721006276

(51) Int. Cl.
| | |
|---|---|
| A61K 9/19 | (2006.01) |
| A61K 47/10 | (2017.01) |
| A61K 47/38 | (2006.01) |
| A61K 35/741 | (2015.01) |
| A61K 35/74 | (2015.01) |
| A61K 49/18 | (2006.01) |
| A61K 39/07 | (2006.01) |
| A61K 31/732 | (2006.01) |
| A61K 9/00 | (2006.01) |
| A61K 47/42 | (2017.01) |
| A61K 35/742 | (2015.01) |

(52) U.S. Cl.
CPC .......... *A61K 35/741* (2013.01); *A61K 9/0056* (2013.01); *A61K 9/19* (2013.01); *A61K 31/732* (2013.01); *A61K 35/74* (2013.01); *A61K 39/07* (2013.01); *A61K 47/10* (2013.01); *A61K 47/38* (2013.01); *A61K 47/42* (2013.01); *A61K 49/1863* (2013.01); *A61K 35/742* (2013.01)

(58) Field of Classification Search
CPC ...... A61K 35/742; A61K 9/0056; A61K 9/19; A61K 47/10; A61K 47/38; A61K 47/42; A61K 35/741; A23K 50/10; A23K 10/18; A23P 10/30; A23L 33/135
See application file for complete search history.

(56) References Cited

U.S. PATENT DOCUMENTS

| | | | |
|---|---|---|---|
| 5,308,615 A | 5/1994 | Deloach et al. | |
| 7,011,826 B1 | 3/2006 | Rowe et al. | |
| 8,114,396 B2 | 2/2012 | Horn et al. | |
| 2014/0010918 A1 | 1/2014 | Quintens et al. | |

FOREIGN PATENT DOCUMENTS

SG    WO 2015/000972 A1 *  1/2015

OTHER PUBLICATIONS

Megastarter (2014, SBIR Phase II: Innovations in manufacturing technology for a probiotic containing Megasphaera elsdenii NCIMB 41125—Megastarter, LLC, 5 pages of PDF).*
Nacheva et al., Bulgarian Journal of Agricultural Science, 2007, vol. 13, p. 153-159.*
Martin MJ, et al., "Microencapsulation of bacteria: A review of different technologies and their impact on the probiotic effects", Innovative Food Science & Emerging Technologies, Feb. 1, 2015, vol. 27, pp. 15-25.
International Search Report and Written Opinion for PCT/IN2018/050062, dated May 30, 2018.

* cited by examiner

*Primary Examiner* — Kade Ariani
(74) *Attorney, Agent, or Firm* — Billion & Armitage

(57) ABSTRACT

The invention relates to a method for the preparation of dry formulations of dairy probiotic bacteria using a combination of different polymers. The said formulations having increased viability during processing, storage and upon transfers to the rumen of the dairy animals. Further said formulations having high tolerance to lactate and acetate in the rumen of dairy animals.

10 Claims, 2 Drawing Sheets

PREPARATION OF DRY FORMULATIONS OF DAIRY PROBIOTICS

FIELD OF THE INVENTION

The invention relates to a method for the preparation of dry formulations of dairy probiotic bacteria using a combination of different polymers. The said formulations having increased viability during processing, storage and upon transfers to the rumen of the dairy animals. Further said formulations having high tolerance to lactate and acetate in the rumen of dairy animals.

BACKGROUND

Cattle are normally adapted to high-concentrate diets. The microbial population which is naturally occurring in the rumen of cattle is normally well suited to digestion of forages. During transition of concentrated diets, opportunistic bacteria produce the lactic acid rapidly and it leads to excesses of lactic acid in the rumen which may cause mild to severe acidosis. The ruminal acidosis (also called lactic acid acidosis) in cattle is of two types, acute or sub acute. During ruminal acidosis, the pH in the rumen drastically drops and remains low for an extended period of time which causes damage in rumen. It occurs when there is a sudden excess intake of highly fermentable carbohydrates, primarily starches and sugars, which produces an excessive amount of lactic acid. The acid gets accumulated due to absence of lactate utilizing bacteria and when the animal is not correctly adapted to the change in diet. The increase of the lactate utilizing bacteria within rumen is one of the preventive measures for the ruminal acidosis.

*Megasphaera elsdenii* is an obligate anaerobic bacterium found in the rumen of ruminant animals. It utilizes lactic acid as a carbon substrate. Lactic acid is produced when the animal or dairy cow is rapidly transferred from a high roughage diet to a high concentrate diet. *M. elsdenii* is dependent on soluble sugars and lactate, produced by other rumen microbes, but is does not produce any acids. In vitro *M. elsdenii* grows well on a variety of substrates such as glucose, fructose, maltose, glucosamine, mannitol, lactate, pyruvate and produces different end products from sugars and lactate. *M. elsdenii* preferentially ferments lactate until low concentrations, 1 to 2 mm, before it utilizes glucose as a substrate. This ability of *M. elsdenii* to preferentially utilize lactate has peaked interest in using this organism as a probiotic for the cattle. Increasing the numbers of lactate-utilizing bacteria in cattle by orally dosing with *M. elsdenii* is useful for reducing the risk of ruminal acidosis in feedlot cattle. This bacterium is orally administered as a feed additive to the cattle but *M. elsdenii* shows their beneficial effect mainly when they are alive. Hence, if they are added to a feed product, they must survive upon consumption of the feed but their survival gets affected during passage through the rumen and at the place of colonization because of extra acidity. So in oral formulations the stability and culture viability is the major concern. *M. elsdenii* being an anaerobic microorganism, its handling, production and maintenance under anaerobic environment for the long term storage is a major concern in developing any probiotic formulations of it.

Various techniques are known to increase the shelf life of the bacteria in commercial formulations. Encapsulation is one known method to increase the shelf life of probiotic formulations. Encapsulation is a process in which tiny droplets or particles are wrapped with a protective coating yielding capsules enclosing the bacteria. Encapsulation of these probiotic bacteria is generally used to enhance the viability during processing, and also for the targeted delivery in rumen. These probiotics are used with the animal feed, pharmaceutical products, and health supplements. They play a great role in maintaining animal health. As the survival of these bacteria in the animal rumen system is questionable so in order to protect the viability of the probiotic bacteria, several types of biopolymers such as alginate, chitosan, gelatin, whey protein isolate, pectin, cellulose derivatives have been used for the encapsulation and several methods of encapsulation such as spray drying, extrusion, emulsion have been reported.

The invention presented herein discloses the method for the development of dry formulations of *M. elsdenii* on a large scale using combination of two different polymers which has a low porosity and which helps in lowering the exposure to unfavourable environmental conditions. It increases the viability during processing and transfer into the rumen of the enclosed bacteria. This encapsulated *M. elsdenii* strain is tolerant to high concentrations of lactate and acetate in rumen of dairy cattle and also utilizes the acid rapidly. This dry powder is easy for handling and transportation and more stable in nature.

BRIEF DESCRIPTION OF THE DRAWINGS

FIG. 2A is the spectrum of pectin. FIG. 2B is the spectrum of carboxymethylcellulose (CMC). FIG. 2C is the spectrum of CMC+pectin mixture. FIG. 2D is the spectrum of CMC+pectin+glycerol mixture enclosing the bacterial cells.

DETAILED DESCRIPTION

Figure 1:
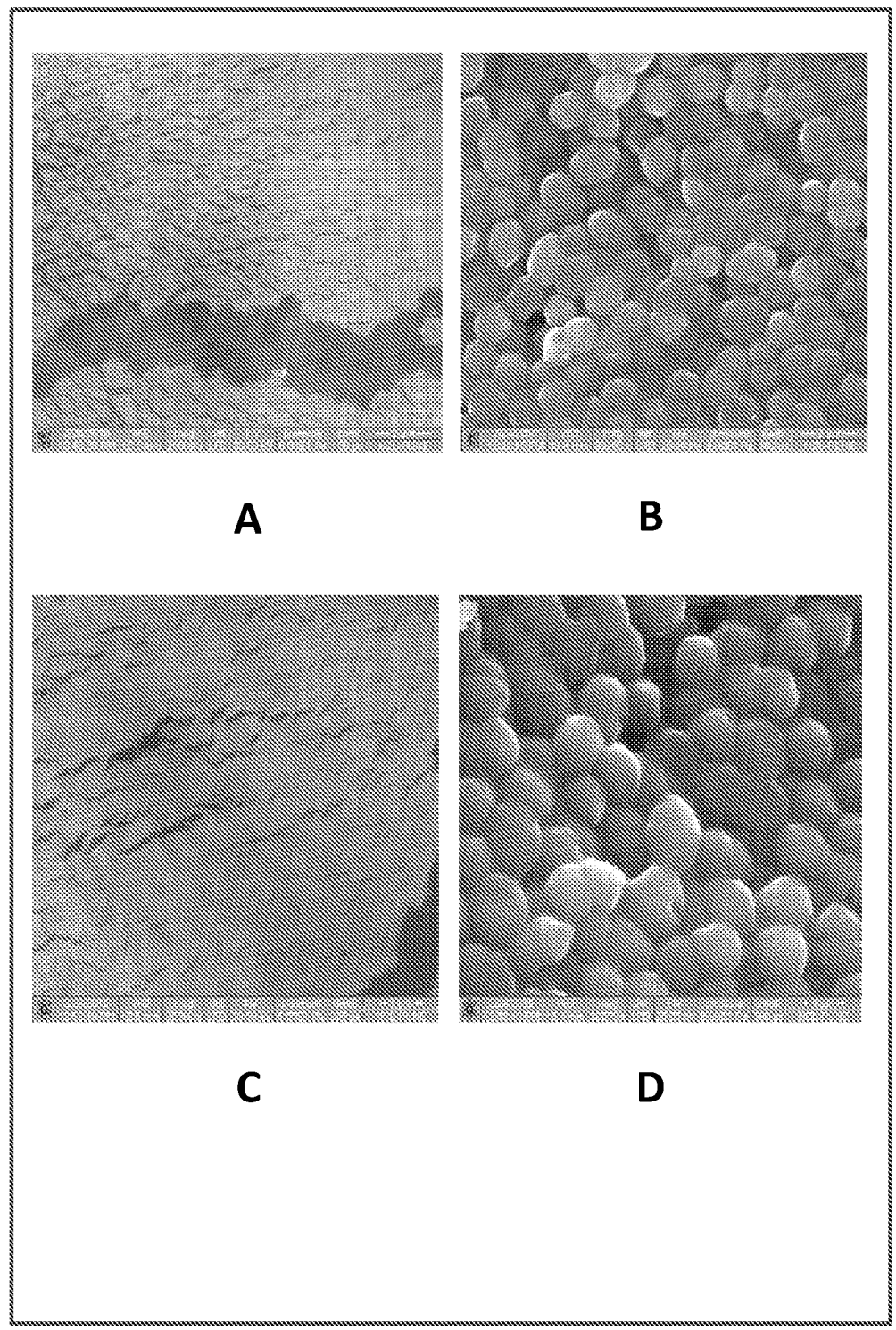
FIGS. 1A-D provide details of the SEM analyses of Example 8. A & C show the encapsulating agent as a powder and B & D show the encapsulating agent enclosing the bacterial cells forming particles of definite size and shape.

A strain of *Megasphaera elsdenii* is used as a probiotic culture for further development of dry solid powder formulations. *Megasphaera elsdenii* is selected on the basis of its tolerance to lactic acid and acetic acid condition and its hydrophobicity. Said culture can attaches well to ruminal walls and preferentially utilizes lactate over other sugars.

In one of the embodiment of present invention, *Megasphaera elsdenii* is cultured in sodium lactate medium in static incubation conditions at about 37° C. for about 24 hours using degassed stoppered bottles. The culture is routinely transferred and stored at about −80° C. in 20% (vol/vol) glycerol stocks between transfers. Said sodium lactate medium is a complex medium with suspended solid in it. For the purpose of the formulation development deMan,-Rogosa-Sharpe (MRS) medium is used, which is simpler and clear growth medium and easy to handle, scale up and for enumeration of microorganisms. The total viable count in MRS medium is about $1.1 \times 10^9$ CFU/ml in static incubation condition at about 37° C. for about 24 hours using degassed stoppered bottles. Said media is selected further for fermentation and for probiotic formulation development. Said *Megasphaera elsdenii* culture is inoculated in degassed MRS broth bottles and incubated in static condition at about 37° C. for about 24 hours. Further said inoculum is inoculated in MRS broth and incubated at static condition for about 24 hours at about 37° C. Further, said broth is subjected to centrifugation with feed rate of about 500 ml/min to separate the wet cake. Next, the wet cake is immediately removed aseptically in LAF unit (Laminar Air Flow) and transferred to an anaerobic chamber. Further about 1% carboxymethylcellulose (CMC) and about 1% of pectin; in combination with 2.5% glycerol is used as an encapsulation agent. Next, encapsulation material and 70% glycerol are sterilized at about 121° C. for about 20 minutes. Further said wet cake, encapsulating chemicals (1% pectin+ 1% CMC) and 2.5% glycerol is mixed properly in anaerobic chamber to prepare a lyoslurry by mixing. Then said prepared lyoslurry is poured in trays and subjected to freezing at about −80° C. for about 2 hours. Post freezing, the frozen lyoslurry is subjected to lyophilisation at about −50° C. for about 28 to about 36 hours to prepare lyopowder. The lyopowder obtained is analyzed for TVC and solids contents. Said broth, wet cake, lyoslurry and lyopowder are serially diluted inanaerobic chamber using sterile degassed saline Tween 80 solution and plated over sterile MRS agar plates. Said plates are incubated at about 37° C. for about 48 to about 72 hours under anaerobic condition. The total solid and TVC values for broth, wet cake, lyopowder and for lyoslurry are enlisted in TABLE 1.

TABLE 1

TVC of *Megasphaera elsdenii* culture at different process stages.

| Sr. No. | Sample | TS (% w/w) | TVC (CFU/gm) |
|---|---|---|---|
| 1 | Harvest/Broth | 04.04 | $5 \times 10^8$ |
| 2 | Wet cake | 23.57 | $1 \times 10^{11}$ |
| 3 | Lyoslurry | 12.75 | $1 \times 10^9$ |
| 4 | Lyopowder | 96.63 | $1 \times 10^7$ |

In another embodiment of the invention, said lyopowder formulations are packed in air-tight containers and stored at room temperature at about 50% relative humidity. The moisture contents of lyopowder formulations are not more than 5% by weight. During storage after specified time periods the TVC analyses are carried out to check the viability of bacteria in the formulations.

In another embodiment of the invention, during the production of dry formulations, *Megasphaera elsdenii* culture survived to oxygenated condition for a short period like centrifugation or serial dilution as checked by measurement of total viable counts. This is important feature as survival of the bacteria in aerobic conditions is necessary for creation of said dry formulations.

In yet another embodiment of present invention, others polymers like hydroxy methyl propyl cellulose, gum acacia, kappa carrageenan, maltodextrin are also tested alone or in combination with or without glycerol as a capsulating agents for rumen bacteria for the preparation of the dry formulations.

Embodiments provided above give wider utility of the invention without any limitations as to the variations that may be appreciated by the person skilled in the art. A non-limiting summary of various embodiments is given above, which demonstrate the advantages and novel aspects of the process disclosed herein.

Advantages

1. Due to use of deMan-Rogosa-Sharpe (MRS) medium for fermentation, the operational expenses are substantially reduced relative to conventional processes.
2. *Megasphaera elsdenii* has hydrophobicity properties which helps them for better attachment in rumen.
3. *Megasphaera elsdenii* has tolerance to lactic acid and acetic acid conditions. Said bacteria can tolerate pH up to 3 and it can also grow well at about 7 pH.
4. Said encapsulation agents used for *M. elsdenii* have a low porosity and which helps in low exposure to unfavourable environmental conditions.
5. The encapsulated dry formulations have increased bacterial viability during processing and transfer to the rumen.
6. The probiotic dry product is more stable and much easier for handling and transport.
7. Due to the powdery nature of probiotic product, the dosage requirements are very low.

Examples provided below give wider utility of the invention without any limitations as to the variations that may be appreciated by the person skilled in the art. A non-limiting summary of various experimental results is given in the examples, which demonstrate the advantageous and novel aspects of the preparation of dry formulations of *Megasphaera elsdenii* using combination of polymers and glycerol.

Example 1

A strain of *Megasphaera elsdenii* (ATCC 25940) was used as a probiotic culture for the development of dry solid powder formulations. The recommended media for *Megasphaera elsdenii* was sodium lactate media. Said culture was grown in sodium lactate medium in static incubation condition at about 37° C. for about 24 hours using degassed stoppered bottles. The culture was routinely transferred and stored at about −80° C. in about 20% glycerol by volume between transfers. The total viable count in sodium lactate medium is about $4.0 \times 10^7$·CFU/ml. Said sodium lactate medium was with suspended solids in it which made it non feasible and it was not useful for scale up and for cell counting by TVC method. Several different media were screened in which deMan-Rogosa-Sharpe (MRS) liquid medium was simpler and clear growth medium and it was easy to handle, to scale up and to count microbial cells. The total viable count in MRS medium was about $1.1 \times 10^9$ CFU/ml in static incubation conditions at about 37° C. for about 24 hours using degassed stopper bottles. So it was selected further for fermentation and for probiotic formulation development.

Example 2: Oxygen Tolerance of *M. elsdenii* During Handling for the Preparation of Dry Formulations About 10 ml culture having initial count of about $4.0 \times 10^7$ CFU/ml was used for the experimentation. About 1 ml culture each was exposed to three different conditions and TVCs were calculated to check the tolerance levels. In one test the culture was serially diluted in laminar air flow [aerobic condition] and then incubated in a glove box for about 37° C. for about 24 hrs and at the end TVC was counted. In second test the culture was serially diluted in anaerobic chamber and then incubated in a glove box for about 37° C. for about 24 hrs and at the end TVC was counted. In third test the culture was centrifuged, wet cake collected and serially diluted [TVC counted in aerobic conditions]; then incubated [anaerobic conditions] in a glove box for about 37° C. for about 24 hrs and at the end TVC was counted. Said three different conditions and its count are enlisted in TABLE 2:

TABLE 2

| Serial Dilution And Plating Condition | Incubation condition | TVC (CFU/ml) |
|---|---|---|
| Aerobic | Anaerobic | $6.0 \times 10^5$ |
| Anaerobic | | $4.0 \times 10^7$ |
| Centrifugation, wet cake serial dilution and plating | | $3.0 \times 10^6$ |

Example 3

The *Megasphaera elsdenii* culture was inoculated in degassed MRS broth bottles and incubated in static condition at about 37° C. for about 24 hours to form a starting culture. Next this starting culture was inoculated in 1.5 l MRS broth and incubated at static condition for about 24 hours at about 37° C. Then said broth was subjected to centrifugation to separate the biomass. Then a pectin solution [an encapsulation agent] having about 1% or 2% concentration were sterilized at about 121° C. for about 20 min. The biomass of *Megasphaera elsdenii* obtained after centrifugation was mixed with sterile pectin solution in 1:1 proportion under the anaerobic condition. Said mixture was mixed well using vortex mixer at low speed to avoid shear disruptions. Said prepared lyoslurry was subjected to freezing at about −80° C. for 2 hours. Post freezing, the frozen lyoslurry was subjected to lyophilisation at about −50° C. about 28 to about 36 hours to prepare the lyopowder. Said lyopowder and lyoslurry were serially diluted in anaerobic chamber using sterile degassed saline Tween 80 solution and plated over sterile MRS agar plates. Said plates were incubated at about 37° C. for about 48 to about 72 hours. Total viable counts analyses of said lyopowder and lyoslurry were carried out in anaerobic chamber to check the encapsulation potential of polymers and loss of viability of probiotic cells after lyophilisation. The total viable counts before lyophilisation (lyoslurry) and after lyophilisation (lyopowder) are given in TABLE 3.

TABLE 3

| Sr. No. | Material | Lyoslurry TVC (cfu/ml) | Lyopowder TVC (cfu/g) |
|---|---|---|---|
| 1 | Control | $6.4 \times 10^9$ | 0 |
| 2 | 1% pectin | | $6.0 \times 10^6$ |
| 3 | 2% pectin | | $6.0 \times 10^6$ |

Example 4

The *Megasphaera elsdenii* culture was inoculated in degassed MRS broth bottles and incubated in static condition at about 37° C. for about 24 hours to form a starting culture. Next this starting culture was inoculated in 1.5 l MRS broth and incubated at static condition for about 24 hours at about 37° C. Then said broth was subjected to centrifugation to separate the biomass. Then a carboxymethylcellulose (CMC), solution [an encapsulation agent] having about 1% or 2% concentration were sterilized at about 121° C. for about 20 min. The biomass of *Megasphaera elsdenii* obtained after centrifugation was mixed with sterile the CMC solution in 1:1 proportion under the anaerobic condition. Said mixture was mixed well using vortex mixer at low speed to avoid shear disruptions. Said prepared lyoslurry was subjected to freezing at about −80° C. for 2 hours. Post freezing, the frozen lyoslurry was subjected to lyophilisation at about −50° C. about 28 to about 36 hours to prepare the lyopowder. Said lyopowder and lyoslurry were serially diluted in anaerobic chamber using sterile degassed saline Tween 80 solution and plated over sterile MRS agar plates. Said plates were incubated at about 37° C. for about 48 to about 72 hours. Total viable counts analyses of said lyopowder and lyoslurry were carried out in anaerobic chamber to check the encapsulation potential of polymers and loss of viability of probiotic cells after lyophilisation. The total viable counts before lyophilisation (lyoslurry) and after lyophilisation (lyopowder) are given in TABLE 4.

TABLE 4

| Sr. No. | Material | Lyoslurry TVC (cfu/ml) | Lyopowder TVC (cfu/g) |
|---|---|---|---|
| 1 | Control | $7.0 \times 10^9$ | 0 |
| 2 | 1% CMC | | $6.0 \times 10^6$ |
| 3 | 2% CMC | | $2.0 \times 10^6$ |

Example 5

The *Megasphaera elsdenii* culture was inoculated in degassed MRS broth bottles and incubated in static condition at about 37° C. for about 24 hours to form a starting culture. Next this starting culture was inoculated in 1.5 l MRS broth and incubated at static condition for about 24 hours at about 37° C. Then said broth was subjected to centrifugation to separate the biomass. Then a solution of 1% carboxymethylcellulose (CMC) and 1% pectin [an encapsulation agent] was sterilized at about 121° C. for about 20 min. The biomass of *Megasphaera elsdenii* obtained after centrifugation was mixed with sterile the CMC+pectin solution in 1:1 proportion under the anaerobic condition. Said mixture was mixed well using vortex mixer at low speed to avoid shear disruptions. Said prepared lyoslurry was subjected to freezing at about −80° C. for 2 hours. Post freezing, the frozen lyoslurry was subjected to lyophilisation at about −50° C. about 28 to about 36 hours to prepare the lyopowder. Said lyopowder and lyoslurry were serially diluted in anaerobic chamber using sterile degassed saline Tween 80 solution and plated over sterile MRS agar plates. Said plates were incubated at about 37° C. for about 48 to about 72 hours. Total viable counts analyses of said lyopowder and lyoslurry were carried out in anaerobic chamber to check the encapsulation potential of polymers and loss of viability of probiotic cells after lyophilisation. The total viable counts before lyophilisation (lyoslurry) and after lyophilisation (lyopowder) were given in TABLE 5.

TABLE 5

| Sr. No. | Material | Lyoslurry TVC (cfu/ml) | Lyopowder TVC (cfu/g) |
|---|---|---|---|
| 1 | Control | $2.0 \times 10^9$ | 0 |
| 2 | 1% CMC + 1% Pectin | | $2.0 \times 10^3$ |

Example 6

Next about 2.5% glycerol was included at the time of preparation of the dry formulation of *M. elsdenii*. The glycerol being moisture retaining agent in the encapsulation agent increased the TVC of the dry formulation significantly as shown in TABLE 6.

TABLE 6

| Encapsulation Agent | Lyopowder TVC (cfu/g) |
| --- | --- |
| 1% CMC + 1% Pectin | $2.0 \times 10^3$ |
| 1% CMC + 1% Pectin + 2.5% Glycerol | $2.0 \times 10^6$ |

Example 7: Shelf Life Study of *M. elsdenii* Lyophilized Powder Formulations

To estimate the shelf life periods for the dry formulations of *M. elsdenii*, they were prepared according to the EXAMPLE 6 and subjected to storage at STP conditions for 30, 60 or 90 days. After the storage periods, the TVC was counted for the each sample and is listed in TABLE 7.

TABLE 7

| Time for storage (days) | Shelf life TVC (cfu/g) |
| --- | --- |
| 0 | $4.0 \times 10^5$ |
| 30 | $3.2 \times 10^4$ |
| 60 | $3.0 \times 10^4$ |
| 90 | $1.0 \times 10^4$ |

Example 8: Analysis of Encapsulated Cells by Scanning Electron Microscopy

To establish the morphology of the particles of the dry formulations of *M. elsdenii* the encapsulating agent [1% CMC+1% pectin+2.5% glycerol] as such and with the bacterial cells enclosed were analysed under a scanning electron microscope. FIG. 1 provides the details of the SEM analyses. FIG. 1 A & C show the encapsulating agent as such as a powdery matter. FIG. 1 B & D show the encapsulating agent enclosing the bacterial cells forming particles of definite size and shape.

Example 9: Infrared Spectral Analyses of Encapsulated Formulations

Figure 2:
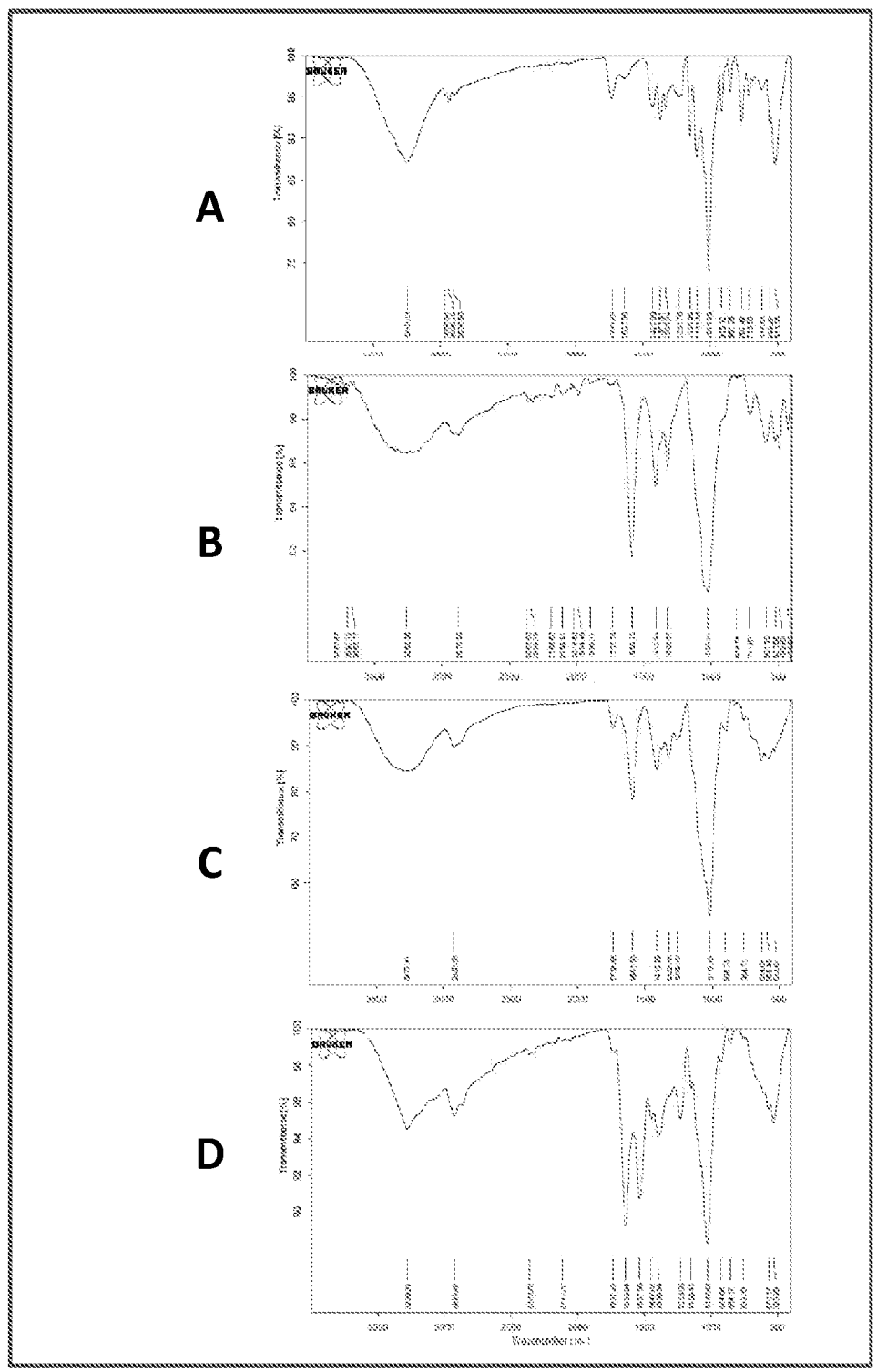
FIGS. 2A-D provide the details the FT-IR analyses of Example 9.

To establish the spectral properties of the particles of the dry formulations of *M. elsdenii* the encapsulating agent components as such and the mixture as such and the mixture with the bacterial cells enclosed were analysed by FT-IR spectrometry. FIG. 2 provides the details the FT-IR analysis. FIG. 2 A is the spectrum of pectin as such. FIG. 2 B is the spectrum of CMC as such. FIG. 2 C is the spectrum of CMC+pectin mixture. FIG. 2 D is the spectrum of CMC+pectin+glycerol mixture enclosing the bacterial cells. The IR spectra were recorded at the wavelength between 4000 cm$^{-1}$ to 500 cm$^{-1}$ with spectral resolution of 4 cm$^{-1}$. The pectin has a sharp absorption at about 1000 cm-1 and CMC has a sharp absorption at 1000 cm$^{-1}$ and at 1600 cm$^{-1}$. After mixing of both pectin and CMC with glycerol, absorption was not changed at these major frequencies and after cell encapsulation, it exhibited absorptions at about 1000 cm$^{-1}$ and at 1600 cm$^{-1}$ and a new absorption at about 1500 cm$^{-1}$, which is remarkable for the encapsulated formulations of the bacteria herein in disclosed.

Embodiments provided above give wider utility of the invention without any limitations as to the variations that may be appreciated by the person skilled in the art. A non-limiting summary of various embodiments is given in the examples and tables, which demonstrate the advantageous and novel aspects of the process disclosed herein.

The invention claimed is:

1. A method for the preparation of dry formulation of anaerobic probiotic bacteria comprising steps of:
    (a) providing a culture of *Megasphaera elsdenii*;
    (b) subjecting said culture to centrifugation to separate bacteria as a wet cake;
    (c) mixing said wet cake with a solution of carboxymethylcellulose, pectin, and glycerol to form a lyoslurry;
    (d) lyophilizing said lyoslurry to encapsulate the *Megasphaera elsdenii* cells in carboxymethylcellulose, pectin, and glycerol and form a lyopowder comprising particles of the encapsulated *Megasphaera elsdenii* cells; and
    (e) packaging said lyopowder in an air-tight container.

2. The method of claim 1, wherein said solution comprises carboxymethlycellulose about 1% by weight.

3. The method of claim 1, wherein said solution comprises pectin about 1% by weight.

4. The method of claim 1, wherein said solution comprises glycerol about 2.5% by weight.

5. The method of claim 1, wherein said lyophilisation is performed at about −50° C. for about 30 to about 36 hours.

6. The method of claim 1, wherein said lyopowder is stable for about 90 days when stored in the air-tight container.

7. The method of claim 1, wherein said lyopowder is suitable for use as a component of animal feed.

8. The method of claim 1, wherein providing the *Megasphaera elsdenii* culture includes culturing in deMan-Rogosa-Sharpe liquid medium.

9. The method of claim 1, wherein the solution has about 1% by weight carboxymethlycellulose, about 1% by weight pectin, and about 2.5% by weight glycerol.

10. The method of claim 9, wherein the solution is mixed with the wet cake at a ratio of 1:1 under anaerobic conditions.

* * * * *